United States Patent [19]

Chermann et al.

[11] Patent Number: 4,547,369
[45] Date of Patent: Oct. 15, 1985

[54] ANTIVIRAL AGENT

[75] Inventors: Jean-Claude Chermann, Garches; Claude Jasmin; Georges Mathe, both of Villejuif; Marcel Raynaud, deceased late of Garches, by Odette J. Raynaud, heir, Versailles, all of France

[73] Assignee: Cabinet Harle & Phelip, Paris, France

[21] Appl. No.: 74,514

[22] Filed: Sep. 11, 1979

Related U.S. Application Data

[63] Continuation of Ser. No. 862,671, Dec. 21, 1977, abandoned, which is a continuation of Ser. No. 639,413, Dec. 10, 1975, abandoned, which is a continuation-in-part of Ser. No. 491,368, Jul. 24, 1974, abandoned.

[30] Foreign Application Priority Data

Jul. 27, 1973 [FR] France ............................ 73 27536

[51] Int. Cl.$^4$ ............................................ A61K 33/24
[52] U.S. Cl. .................................................. 424/131
[58] Field of Search ........................ 424/131; 423/593

[56] References Cited

FOREIGN PATENT DOCUMENTS

2435746 2/1975 Fed. Rep. of Germany ...... 423/593

Primary Examiner—Jerome D. Goldberg
Attorney, Agent, or Firm—Bierman, Peroff & Muserlian

[57] ABSTRACT

Compounds containing the heteropolyanion 9-antimoni-III-21-tungsto VI sodate of the formula [NaSb$_9$W$_{21}$O$_{86}$] preferably the ammonium, alkali and alkali metal salts thereof, are active when administered by injection against virus infections, particularly leukemia, sarcoma and encephalomyocardia virus, as shown, by tests in vitro and in vivo in mice.

5 Claims, 2 Drawing Figures

FIG.2

ANTIVIRAL AGENT

PRIOR APPLICATION

This application is a continuation of copending patent application Ser. No. 862,671 filed Dec. 21, 1977, now abandoned, which is turn is a continuation of copending application Ser. No. 639,413 filed Dec. 10, 1975, now abandoned, which in turn is a continuation-in-part of our copending, commonly assigned U.S. patent Serial No. 491,368 filed July 24. 1974 now abandoned.

The present invention, which results from work carried out by the Institut Pasteur or by direction of the latter, has for its object a compound of complexed heteropolyanions which contains tungsten combined with antimony. The invention is more particularly concerned with a compound and its application as a medicament for the curative and preventive treatment of diverse viral infections.

The compound according to the invention is characterized by the fact that it contains a heteropolyanion in which the central atom is antimony while the ligand groups grouped around said central atom are tungsten ions bound to one another by bridges of oxygen atoms.

To illustrate the prior technique in the field of heteropolyanions, one may refer to the works of P. Souchay entitled "Ions mineraux condenses" (Masson et Cie., Edit-Paris (1969)) and "Polyanions et Polycations" (Gauthier-Villars, Edit-Paris (1963)). These general works, nevertheless, do not contain any indications of obtaining heteropolyanions in which the central atom is antimony. The chemical definition of 2-antimonio-5-tungstate (III) and its obtention are indicated in the article of C. R. Academie des Sciences, Paris, volume 274, Jan. 17, 1972, pages 209–212.

However, it has just recently been ascertained by infrared and Raman spectra that the said product has a formula different from that assigned to it and the said heteropolyanion has the actual formula of $[NaSb_9W_{21}O_{86}]^{18-}$ The heteropolyanion compound according to the invention is at the same time a complex compound and an acid salt. It may be present as such or in the form of ammonium salts or salts of metals, in particular alkali metals and alkaline earth metals.

As has been already indicated, the heteropolyanions are inorganic ions obtained by condensation of tungsten W around a central ion which is antimony Sb. The heteropolyanion compound according to the present invention is thus a antiomonio-III-tungstato VI sodate.

The heteropolyanions, as far as is known, possess numerous hydrates. All the hydrated forms of antiomonio-tungstate enter into the scope of the present invention.

The heteropolyanions are characterized by the series to which they belong in defining the ratio $r = W/Sb$. In the "11 series" the ratio r is equal to 11. The preparation and the physico-chemical properties of the 11-tungstoantimoniates (III) and 11-tungstobismuthates (III) are described in the article by P. Souchay, Vol. 271, pages 1337 to 1340, (30th Nov. 1970)).

The present invention has particularly for its object the utilization of 9-antimonio-III-21-tungsto VI sodate which is a heteropolyanion compound comprising, in the centre, nine antimony atoms Sb and around the said atoms, 21 atoms of tungsten, the characteristic ratio r being thus equal to about 2.4.

The invention covers also in their entirely all isomeric forms as exist of the heteropolyanion in question.

The invention extends to the heteropolyanion compound itself as well as to mixtures obtained by transformation of the said antimonio-tungstate under the influence of variations of pH. The new heteropolyanion compound according to the invention, namely 9-antimonio-III-21-tungsto-VI sodate is stable at a pH of 6.5 to 7, that is to say in the neighborhood of neutrality. This property is particularly advantageous in the application of the said compound as a medicament which will be illustrated hereafter.

For the purposes of the present invention it is interesting that the heteropolyanion compound is presented in the form of pharmaceutically acceptable metallic salts. In preference there will be chosen the salts formed with alkali or alkaline earth metals including ammonium salts. The salts currently used are the salts of sodium, potassium and ammonium. The heteropolyanion compound may also if necessary be utilized as such or in acid form.

To obtain 9-antimonio-III-21-tungsto VI sodate in the form of its ammonium salts, an aqueous solution containing the ion $Sb^{III}$ is caused to react with heat with a 1M solution of sodium tungstate, the reaction medium being kept substantially at neutrality by the addition of concentrated ammonium hydroxide in sufficient quantity to render the medium colorless, which brings about the precipitation of the desired ammonium salt which one recovers by filtration and then treats in usual manner.

The temperature of the reaction is lower than the boiling temperature of the reaction medium, for example, in the neighborhood of 80° C. The aqueous solution containing the ion $Sb^{III}$ is advantageously prepared by dissolving $SbCl_3$ in a saturated solution of $NH_4Cl$.

The final compound is ammonium 9-antimonio-III-21-tungsto VI sodate. Its pH in aqueous solution is in the neighborhood of 6.7. The salts occurs in the form of a hydrate of formula $[NaSb_9W_{21}O_{86}](NH_4)_{18} \cdot 8H_2O$ In aqueous solution the salt occurs as a tetramer.

In the following description this last compound will be designated indifferently by the abbreviations TA or HPA23.

The antimoniotungsto sodate of the invention is active in the preventive or curative treatment of certain viral affections in man and animal. It will be recalled that, in French Pat. No. 70.45.843 of the 18th Dec. 1970 and in its first certificate of addition No. 71.43.444 of 3rd Dec. 1971, there has already been described the application, as an antiviral medicament, complex compounds of heteropolyanions containing tungsten. However, although the compounds described in these two documents are medicaments of value for certain viral affections, their active in vivo on leukemia and sarcoma viruses proves insufficient. An already known and particularly efficacious heteropolyanion is sodium tungstosilicate. This later compound possesses a direct viralicidal action it becomes fixed to the virus, thus produces a solubilization of the viral material. Thus, sodium tungstosilicate acts by pretreatment of the cells as well as during viral adsorption. It is highly probable that the action of sodium tungstosilicate is on the cellular membrane. In a quite unexpected manner, it is now found that 9-antimonio-III-21-tungsto sodate (TA) is capable of protecting mice against leukemias induced by Friend's virus and plasma variant described by Mr CHIRIGOS. When the product is injected the day of inoculation with virus, there can be obtained either a complete protective effect without detectable leukemia, or a partial protection, as shown by a reduction of the mean weight of the spleen, a diminution in the titre of virus in the plasma and the spleen, and an augmentation in the mean survival time. Mice can be immunized against the leukemia virus of Friend by the simultaneous injection of virus and TA.

When the treatment is commenced 3 to 7 days after inoculation of the virus, in two experiments out of four, a significant reduction in the mean weight of the spleen has been obtained after treatment with TA and also an increase of the survival time. TA is also capable of retarding the appearance of tumors in new-born mice inoculated with virus M-MSV.

TA does not induce interferon and has no effect on graft leukemia. Its action does not necessitate direct action between the virus and the product. Pharmacological trials will be reported in more detail hereinafter. The exceptional properties of TA were absolutely unforeseeable by a man skilled in the art.

In cell culture studies:

Ammonium antimoniotungsto sodate acts neither by pretreatment nor during the period of adsorption of the virus. The antimoniotungsto sodate penetrates the cell as can be seen in the electron microscope (the tungsten part of the heteropolyanion is opaque to electrons), or by the use of labelled antimoniotungstate when it is recovered in certain cell fractions, notably in the nucleus. It acts during the first 24 hours after viral adsorption, but also belatedly between the 48th and the 72nd hour. A more precise study has shown that the action of the antimoniotungsto sodate occurs between the 69th and 72nd hour.

The antimoniotungsto sodate strongly inhibits the enzyme activity of RNA dependent DNA-polymerase of the sarcomatogenic and leukemogenic viruses (oncornavirus).

The 50% inhibitory dose of antimoniotungsto sodate is 1.25 $\mu$g/ml of reaction mixture. The enzymatic reaction is stopped immediately on the addition of the antimoniotungsto sodate.

The inhibition by the 9-antimonio-III-21-tungsto VI sodate is of the competitive type. It is possible to overcome the inhibition by addition of hybrid r A-oligo dT, but not by poly rA alone, oligo dT alone or the viral enzyme. The antimoniotungsto sodate does not fix to model rAdT nor to proteins, nor to nucleic acids.

In vivo-Animal experiments:

9-antimonio-III-21-tungsto VI sodate reduces the development of splenomegaly induced by Friend's virus and the "Plasma variant" of Chirigos. Likewise, it retards the appearance of tumors by the Moloney virus in new-born mice. Its activity is identical with or even superior to that of interferon, inducers of interferon or other antiviral products used in comparable experimental conditions. Experiments have shown that this product is not an inducer of interferon. It is active in three types of malady: an erythroblastic leukemia, an undifferentiated leukemia and a muscular sarcoma; its effect is not specific to a target cell. Its activity does not necessitate direct contact with the virus and the possibility of an inhibition of transport of virus from the peritoneal cavity to the blood is eliminated by the inhibitory action observed when the virus is inoculated by the intravenous route.

The invention also provides a method for the treatment, prevention or prophylaxis of viral infections in mammals comprising the administration by injection of a sterile solution of a clinically effective amount of the 9-antimonio-III-21-tungsto VI sodate.

There will now be described by way of illustration a precise example of obtaining the product TA in the form of its ammonium salt.

EXAMPLE

Preparation of $[NaSb_9W_{21}O_{86}](NH_4)_{18}$

There was added an aqueous solution containing the ion $Sb^{III}$ and obtained by dissolving 11.4 g of $SbCl_3$ in 50 ml of a saturated solution of $NH_4Cl$, to 125 ml of an aqueous 1M solution of sodium tungstate warmed to 80° C. Just before the end of the addition of the solution containing the $Sb^{III}$ ion, there was added a sufficient quantity of concentrated ammonium hydroxide to render the reaction medium colorless. The ammonium salt of the precipitated heteropolyanion was filtered, washed with a dilute solution of $NH_4Cl$ and finally crystallized from distilled water. The compound obtained is pure ammonium 9-antimonio-III-21-tungsto VI sodate [hereafter calld HPA 23]. In aqueous solution it occurs in the form of a tetramer. The aqueous solution possesses a pH in the neighborhood of 6.7. It is stable in aqueous solution in the neighborhood of pH 7. In the natural state it occurs in the form of a white powder very soluble in water. The crystallized product is stable without modification at room temperature. For the purpose of pharmacological tests it is dissolved in physiological saline (aqueous solution of NaCl 0.9%) before being used.

Figure 1:
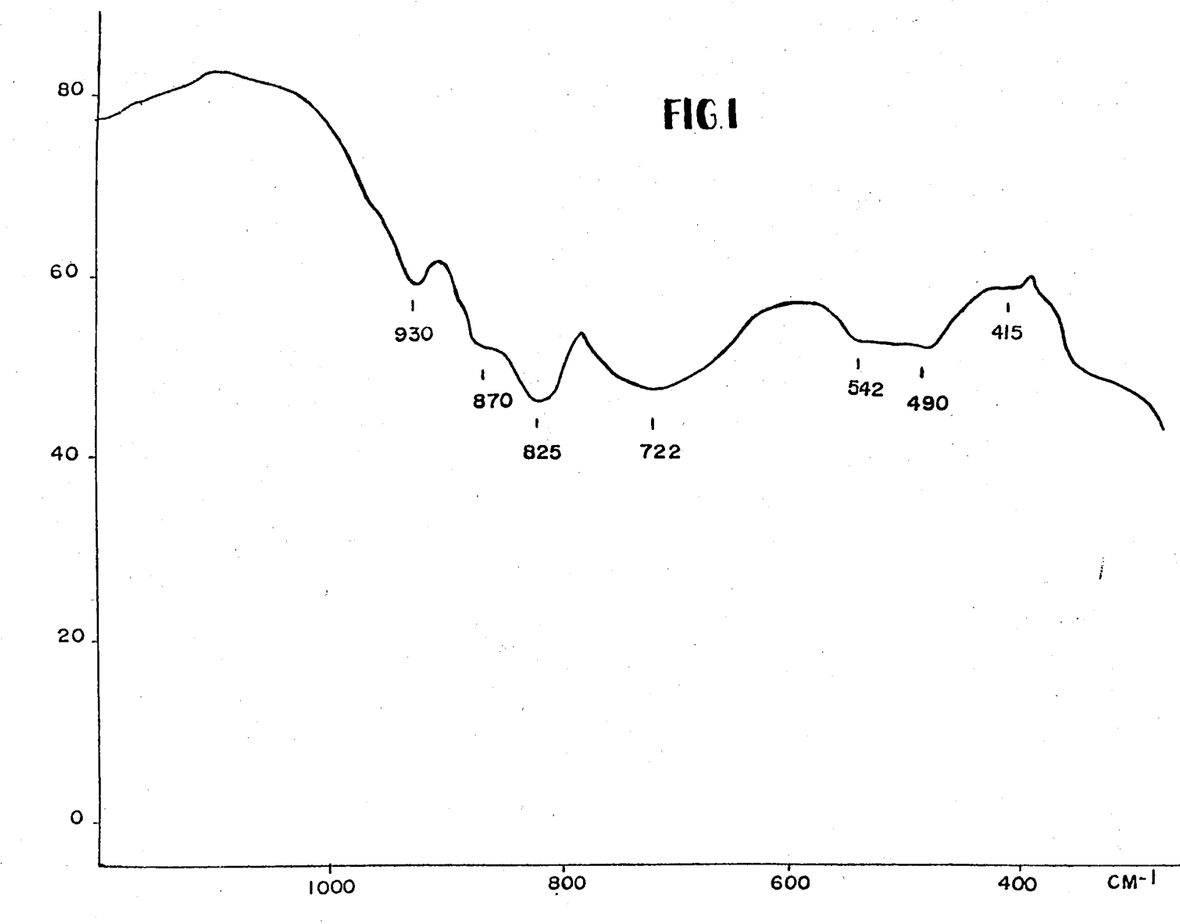
Figure 2:
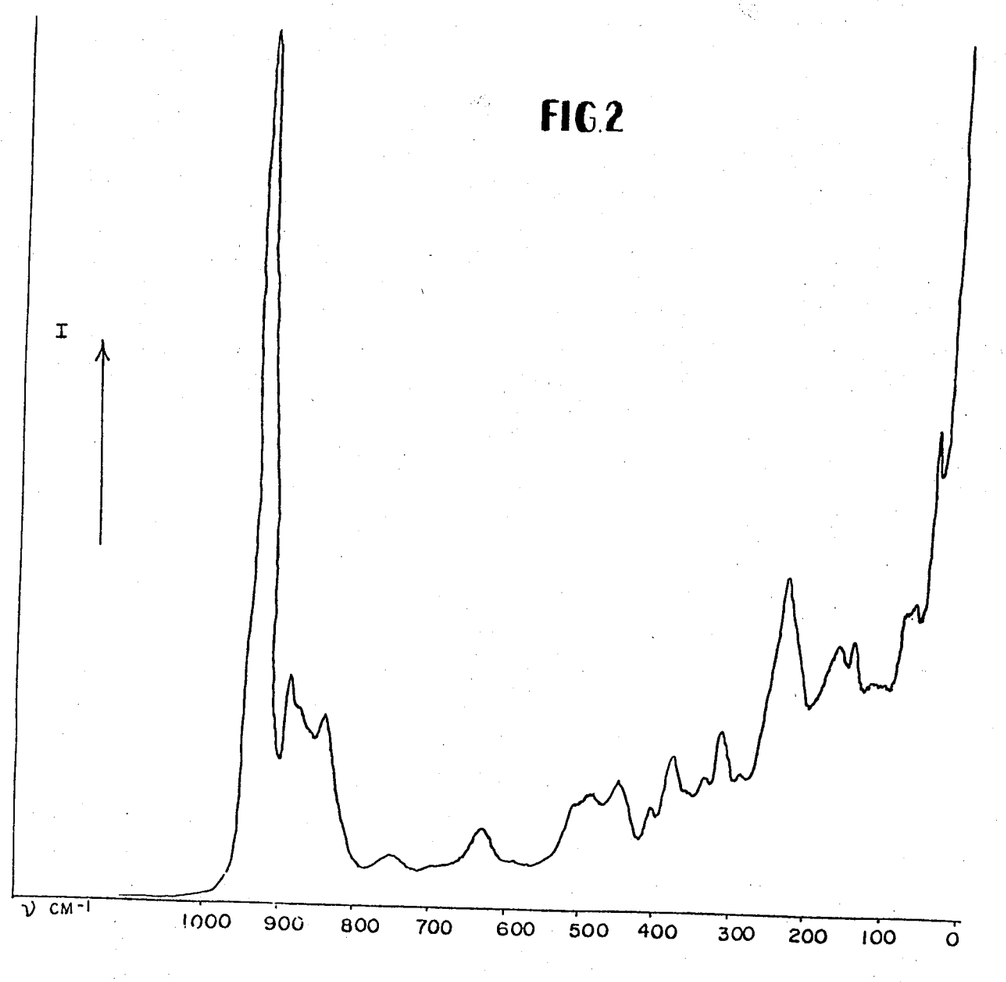

FIG. 1 is the infrared spectrum of the product in potassium chloride solution and FIG. 2 is the Raman spectrum of the product. At a pH of 7.5 in a buffered 0.5M Tris and 0.5M NaCl solution, the product showed two vague reduction polarographs with a potential of $-1.11$ and $-1.22$ volts with respect to a saturated calomel electrode.

To obtain ammonium 9-antimonio-III-21-tungsto VI sodate labelled by antimony 125, one proceeds as follows:

A saturated solution of ammonium chloride ($NH_4Cl$) containing 2 ml of labelled antimony chloride (0.53 mCi/ml) and 0.278 g of unlabelled antimony chloride is added hot (about 60° C.) to 3 ml of sodium tungstate solution (0.33 g/ml). The ammonium salt of labelled 9-antimonio-III-21-tungsto VI sodate precipitates in the course of the preparation and continues to come out in the course of cooling. The precipitate is filtered, washed with a solution of $NH_4Cl$, then recrystallized from water; it is then dried over phosphoric anhydride in vacuum and recovered.

I. Effect of the heteropolyanion HPA 23 on Friend's leukemia

Tests have been made on mice infected with Friend's leukemia. After the injection of a predetermined dose of the virus responsible for this disease, one records the death of all the mice generally between the 30th and the 40th day. Comparatively, there is injected 0.5 mg per mouse of the product HPA 23 on the second day following the day of viral injection. The results are collected in the following Table.

TABLE 1

| HPA | VFA | Treatment of Friend's leukemia | |
|---|---|---|---|
| | | $5 \times 10^{-4}$ | $10^{-4}$ |
| HPA 23 | day 0 | 0.923 g | 0.686 g |
| | day 1 | 1.660 g | 1.827 g |
| | days 1, 7, 14 | 2.226 g | 1.566 g |
| | days 0, 7, 14 | 0.647 g | 0.643 g |
| | Control virus | 2.547 g | 2.013 g |

It is found that, according to the results of Table 1, one injection of the product HPA 23 given after the viral injection results in a very clear diminution of the splenomegaly, which indicates a regression of the leukemia.

II. Toxicological study of the product HPA 23:

The toxicological study of the product "HPA 23" has been carried out in four species of animals:
the tricolored guinea pig;
the white New Zealand rabbit;
the beagle;
the mouse.

The product HPA 23 was given in the form of a solution in physiological saline.

ON GUINEA PIG

The experiment lasted 42 days in the course of which the product was administered in increasing doses varying between 2 and 15 mg/Kg day by subcutaneous and intravenous routes.

ON RABBIT

The study was pursued for 42 days.
The product was injected by the endovenous route in increasing doses varying between 2 and 32 mg/Kg/day.

ON DOG

The product was likewise administered by the intravenous route for 21 days in increasing doses varying between 20 and 100 mg/dog/day.

In the experimental conditions described above, the product "HPA 23" was well tolerated by the experimental animals: the guinea pig, the rabbit and the dog.

There must be noted, however, an adverse phenomenon in the guinea pig when the product is administered by the subcutaneous route in the form of a local necrotic phenomenon consequent upon these injections. For this species, the intravenous route appears much better.

In the rabbit, there have likewise been raised some necroses, near the veins.

For the three species, the general tolerance was good, the product having been injected:
for 42 consecutive days in the guinea pig and the rabbit;
for 21 days in the dog.

At the end of the experiments, all the animals were sacrificed and the organs were examined from the histological and anatomical point of view. Nothing abnormal was noticed which permits drawing the conclusion that there is good tolerance of the product.

Each of the animals was followed from the point of view of change of weight and of temperature. For dogs, a daily renal and hepatic balance-sheet was made. All these factors were normal.

III. Study of the anti-viral power of the product HPA 23

The following tests have been used:
(a) in vitro:

($a_1$) Inhibition of the formation of foci of infection or plaques by the sarcomatogenic virus of Moloney on fibroblasts of embryo mice.

($a_2$) Inhibition of the replication of the leukemogenic virus (Test X, C according to ROWE, P. W. et al., Virology, 1970, 42, 1136).

($a_3$) Inhibition of the polymerization reaction of RNA dependant polymerase regulated by DNA, according to KAPULER, A. M. et al., Nature 1970, 225, 1209.

(b) in vivo:
on Friend's leukemia;
on the leukemia obtained by inoculation of "Plasma variant" of Chirigos;
on the formation of tumors in new-born mice by Moloney's sarcomatogenic virus.

The leukemiogenic power and the development of the disease are followed by in two different ways:
either the removal of the spleens of the animals on the 21st day after the inoculation of the virus and comparison of the weights of the spleens of treated and untreated animals;
or by measuring the time of survival of treated animals in relation to non-treated animals.

Inhibiting properties "in vitro" of the product HPA 23

(I) Inhibition of the formation of foci of transformation or plaques.

The inhibitory dose 50 to 100 ($ID_{50}$) calculated by the method of Reed and Muench is 15 μg/ml average.

(a) there is no direct virulicidal action on the virus: in effect if the virus and the antimoniotungstate (TA) are left in contact in increasing doses for 1 hour at 0° C., a lowering of titre is not observed, but on the contrary, an activation (see Table 2).

(b) there is no fixation of the antimoniotungstate on the virus:

If one uses antimoniotungstate $125_{Sb}$ and contacts the virus with the labelled antimoniotungstate and centrifuges the mixture on a density gradient (5 to 55 percent saccharose), the virus attains equilibrium (1.14–1.15 g/ml) and is not markedly radioactive: it has not therefore fixed the antimoniotungstate.

TABLE 2

| CONTACT OF VIRUS - ANTIMONIOTUNGSTATE | | | Focus forming units |
|---|---|---|---|
| Virus | | 1 hour at 0° C. + 4° C. | 44 |
| Virus + TA | 1 mg/ml | 1 hour at 0° C. + 4° C. | 85 |
| Virus + TA | 2 mg/ml | 1 hour at 0° C. + 4° C. | 65 activation |
| Virus + TA | 5 mg/ml | 1 hour at 0° C. + 4° C. | <<106 |
| Virus + TA | 10 mg/ml | 1 hour at 0° C. + 4° C. | Too numerous to be counted |

(c) Ammonium antimoniotungstate is not toxic for cells at inhibitory doses: cellular growth is not affected in the presence of antimoniotungstate: the same number of cells are recovered from the treated flasks as from the untreated flasks, the same profile as far as concerns the incorporation of tritiated thymidine (synthesis of DNA), of tritiated uridine (synthesis of RNA), of seleno-75-methionine (for protein synthesis).

(d) Antimoniotungstate does not act in pretreatment, nor during absorption of the virus. The best protective effect is obtained if the product is added after the viral infection.

(II) Inhibition of the formation of syncytia (Text XC)

The 50 percent inhibitory dose is on average 16 μg/ml (see a typical experiment in Table 3).

(III) Inhibition of the reaction of polymerisation of RNA dependant polymerase regulated by DNA, according to KAPULER, A. M. et al., Nature,1970, 225,1209 experimental protocol according to D. Baltimore;
exogenous reaction: primer oligo d T, template or Ag
$ID_{50}$: 1.4 μg/ml of reaction medium;
immediate arrest of the polymerisation reaction from the moment of the addition of antimonio-tungstate;

The inhibition is not reversible: if one incubates a solution of enzyme with a dose of heteropolyanion giving an inhibition of 50 percent and if one dilutes to 1/10, the speed of the reaction is not modified, signifying that the inhibition is reversible.

The antimoniotungstate:
inhibits polymerases;
is without reaction on ribonucleases and desoxyribonucleases;
is without action on proteases (pronase, pepsin, trypsin);
does not fix on to proteins (albumin) inhibits RNA dependent DNA polymerase of murine oncornavirus.

TABLE 3

| Sample | Dose γ/ml | TEST XC Mean syncitium | Percent Inhibition | $ID_{50}$ γ/ml |
|---|---|---|---|---|
| Control | | 35 | 0 | |
| Antimonio-tungstate (TA) | 40 | 9 | 74 | 16 |
| | 20 | 15 | 57 | |

(IV) Inhibitory action of antimoniotungstate on different viruses of the Oncornavirus group:

(a) Rabies virus
Experiments give the following results:
$ID_{50}$: 4 μg/ml;
no direct action on the virus;
non-toxic for cells at the doses used.

(b) Other viruses:
Product HPA 23 is active in vitro on other viruses, such as the vesicular stomatitis virus (VSV), the encephalomyocarditis virus of mice among others.

Inhibitory properties "in vivo"

It has already been shown that ammonium antimoniotungstate has a very strong antiviral activity "in vitro". Some trials have been conducted to put in evidence the antiviral activity "in vivo". For that purpose, appeal has been made to experimental leukemias in mice, Friend's leukemia, leukemia induced by the "plasma variant" of Chirigos where mesurements of leukemia may be effected:

(1) by the degree of splenomegaly on the 21st day,
(2) in measuring the survival of animals having received or not received antimoniotungstate.

Table 4 shows the antiviral activity of antimoniotungsto on the two types of leukemia, the product being injected 30 minutes before the virus (the strong diminution of the splenomegaly is to be noted). It is probably a matter of a diminution of the production of virus in the spleen or in the plasma of treated mice in comparison with control mice, as one recovers very little virus (table 5).

In table 6, there are reported experiments in which the dose of antimoniotungstate is varied, and it will be seen that an excellent protection can be obtained up to 10 μg per mouse (1 single injection).

Table 7 shows that it is not necessary that the virus and the product should be injected by the same route to obtain an effect. Only the oral route is ineffective (experiment 5).

Table 8 shows that the protected animals are immunised against the virus. Thus if a new dose of virus is injected into treated and protected mice, it is shown that the animals do not develop the disease.

If the survival of the animals is studied, it becomes clearly established that all the control animals are dead on the 30th day. Most of the treated animals survive until the 85th day. The plasma and spleen of the surviving animals has been taken and after innoculation into normal mice, it is observed that these mice do not develop leukemia. The treated animals were thus cured.

It has equally been determined that the treatment may be efficacious if it is applied after the development of the illness. There is good protection if the product is injected on days 2, 4, 6, 8 or again in the form of a single injection on the 10th day or several on days 14, 16, 18, 20.

From other experiments there has been shown the delay in the appearance of tumors induced by Moloney's sarcoma in new-born mice. Finally, antimoniotungstate protects mice against a 100 percent lethal dose of EMC virus (encephalomyocarditis).

CONCLUSION

Ammonium 9-antimonio-III-21 tungsto VI sodate possesses a broad antiviral spectrum, is active "in vivo" and is well tolerated.

The foregoing detailed results show clearly the efficacy of the heteropolyanion compound containing tungsten combined with antimony in the treatment of viral infections. Thus the product TA or HPA 23 is an antiviral medicament of value. It is particularly active in vivo on leukemogenic and sarcomatogenic viruses. It is also active in vivo on encephalomyocarditis virus. (vesicular stomatitis virus).

Administration is carried out by injection. A suitable form of dosage is in unit dosage form in sterile ampules containing medicinal amounts. The active compound may be associated with a vehicle suitable for injection. In veterinary applications the carrier may be an aqueous solution or a mineral oil. For man aqueous solutions in 0.9% NaCl are preferred which are suitable as an administrative vehicle in the neighborhood of neutral pH, the active compound being perfectly soluble in such a solution.

TABLE 4

| Effect of 21-tungsto-9-antimoniate on leukemias produced by Friend's viruses (FLV) and by "Plasma variant" (PV) | | | | |
|---|---|---|---|---|
| Viruses inoculated | Experiment | Treatment* | Mean weights of the Spleen (mg) | Statistical significance (p) |
| FLV | 1 | WITHOUT TREATMENT | 1,250 | |
| | | 2 mg | 254 | 0.001 |

TABLE 4-continued

Effect of 21-tungsto-9-antimoniate on leukemias produced by Friend's viruses (FLV) and by "Plasma variant" (PV)

| Viruses inoculated | Experiment | Treatment* | Mean weights of the Spleen (mg) | Statistical significance (p) |
|---|---|---|---|---|
| FLV | 2 | 1 mg | 235 | 0.001 |
| | | WITHOUT TREATMENT | 2,814 | |
| | | 2 mg | 327 | 0.001 |
| | | 1 mg | 267 | 0.001 |
| PV | 3 | WITHOUT TREATMENT | 607 | |
| | | 2 mg | 166 | 0.001 |
| | | 1 mg | 228 | 0.001 |

*One injection by the i.p. route of 5-tungsto-2-antimoniate was administered ½ hour before the inoculation of the viruses.

TABLE 5

Titration of Friend's leukemia viruses in the plasma and in the extracts of spleen

| Groups | Mean weight of the Spleen (mg) | Titre of the viruses/0.2 ml in the plasma | Titre of the viruses/0.2 ml in the spleen |
|---|---|---|---|
| without treatment | 2.584 | $10^5$ $SD_{50}$ | $10^{4.2}$ $SD_{50}$ |
| treated with 2 mg of TA | 245 | $10^{1.36}$ $SD_{50}$ | $10^2$ $SD_{50}$ |

TABLE 6

Relation dose/effect of 21-tungsto-9-antimoniate on Friend's leukemia

| Experiment | Treatment* | Mean weight of the Spleen (mg) | Statistical significance (p) |
|---|---|---|---|
| 1 | no treatment | 1,201 | |
| | 2 mg | 278 | |
| | 1 mg | 221 | 0.001 |
| | 0.5 mg | 237 | 0.001 |
| | 0.2 mg | 239 | 0.001 |
| 2 | no treatment | 2,195 | |
| | 0.5 mg | 234 | 0.001 |
| | 0.2 mg | 228 | 0.001 |
| | 0.1 mg | 199 | 0.001 |
| | 0.05 mg | 290 | 0.001 |
| 3 | no treatment | 1,350 | |
| | 2 mg | 208 | 0.001 |
| | 1 mg | 292 | 0.001 |
| | 0.5 mg | 314 | 0.001 |
| | 0.1 mg | 345 | 0.001 |
| | 0.05 mg | 376 | 0.001 |
| | 0.01 mg | 361 | 0.001 |

*The products TA and the viruses were inoculated by the i.p route on day 0

TABLE 7

Study of the routes of injection of 21-tungsto-9-antimoniate and of Friend's leukemia viruses

| Experiment No. | Route of inoculation of the viruses | Route of administration of TA | Mean weight of the spleen |
|---|---|---|---|
| 1 | I.P. | No treatment | 2,814 |
| | | i.p. | 639 |
| | | i.p. | 334 |
| | | sub-cutaneous (s.c) | 1,030 |
| | | intra-muscular (i.m.) | 599 |
| 2 | I.P. | No treatment | 932 |
| | | i.p. | 283 |
| | | i.p. | 349 |
| | | i.m. | 341 |
| | | s.c. | 348 |
| 3 | I.P. | No treatment | 1,245 |
| | | i.p. (mixed with the viruses) | 205 |
| | | i.p. (separately) | 235 |
| 4 | I.V. | I.P. | 240 |
| 5. | I.P. | No treatment | 2,638 |
| | | 5 mg per day mixed with the food | 2,370 |

The product TA was administered on day 0. In all the experiments, except No. 5, one single injection of 1 mg of product was used. The injections i.p. route were made ½ hour before the inoculation of the viruses, except in experiment No. 3

TABLE 8

Resistance of mice pretreated with the Friend's leukemia viruses (FLV) and 21-tungsto-9-antimoniate against a challenge dose of FLV

| Exp. No | Pretreatment | Inoculation of the challenge viruses (dose and day) | | Mean weight of the spleen 3 weeks after the challenge dose |
|---|---|---|---|---|
| 1 | No treatment | 50 $SD_{50}$ | on the 21st day | 2,199 |
| | | 10 $SD_{50}$ | | 2,251 |
| | | 5 $SD_{50}$ | | 1,754 |
| | Injection i.p. on day 0 of 20 $SD_{50}$ of FLV of 2 mg TA | 20 $SD_{50}$ | on the 21st day | 509 |
| | | 10 $SD_{50}$ | | 403 |
| | | 5 $SD_{50}$ | | 363 |
| 2 | No treatment | 10 $SD_{50}$ | on the 42nd day | 2,554 |
| | | 5 $SD_{50}$ | | 1,623 |
| | | 2.5 $SD_{50}$ | | 445 |
| | Injection i.p. on day 0 and on day 21 of 20 $SD_{50}$ of FLV and of 2 mg of TA | 10 $SD_{50}$ | on the 42nd day | 393 |
| | | 5 $SD_{50}$ | | 304 |
| | | 2.5 $SD_{50}$ | | 227 |

According to an advantageous mode of administration, the aqueous solution of the active compound has added to it insoluble calcium phosphate, for example at a dose of 5 mg/ml of solution.

Tests on mice have shown that in this manner there is prepared a delay medicament.

The product HPA 23* (radioactive form) coupled to calcium phosphate in aqueous solution with 0.9% NaCl was injected by the intraperitoneal route into mice. One mouse was sacrificed each day and the localization of the product was determined. The greatest part of the product was found in the liver (hepatic localization), a relatively important part in the kidneys and a less important part in the lungs. In these conditions, the product persists for more than 15 days in the animal organism. In the absence of calcium phosphate the product is eliminated, practically in 5 hours. On the contrary, when calcium phosphate is added, it passes very progressively among the organs and its elimination in the urine is found to increase with time.

The invention is not limited by the foregoing detailed indications. Salts of 9-antimonio-III-21-tungsto VI sodate can be utilized as active agents in pharmaceutical compositions applicable in a large range of viral infections for preventive or curative treatment. These medicaments may be associated with other agents possessing an antiviral activity. Ammonium 21-tungsto-9-antimoniate (AmTA) has been shown above to be active in vitro and in vivo against murine leukemia and sarcoma viruses. AmTA has also a broad in vitro antiviral activity and protects mice against murine encephalomyocarditis viral infections.

The in vitro activity of AmTA on cytopathic effects induced by various RNA and DNA viruses was studied in monkey kidney and human WI-38 cell cultures grown in BME with 10% calf serum.

In monkey kidney and human WI-38 cell cultures, the highest non-cytotoxic concentration of AmTA was 125 $\mu$g/ml of medium, when added to confluent monolayers; no inhibition of cellular growth was observed when the compound was added at 30 $\mu$g/ml to the cultures at the time of seeding. When the cultures were treated about 1 hour before virus inoculation with concentrations of AmTA ranging between 15 and 125 $\mu$g/ml, a marked inhibition of the cytopathic effect (CPE) of several DNA and RNA viruses was obtained: Table 9 summarizes the results, expressed as "virus ratings" and inhibiting doses 50% (4); the coefficient VR measures the inhibition of the cytopathogenic effect of the virus by the tested compound at different concentrations, starting from the highest-non-cytotoxic dose. The kinetics of the inhibitory activity were studied on Herpes simplex virus (HF): (a) when the compound was added at 30 $\mu$g/ml 1 hour before virus inoculation and left in the cultures thereafter, it was highly active: 3.5 $\log_{10}$ reduction of virus titer at 24 hours; (b) if, however, the cultures were treated for 2 hours with 125 $\mu$g/ml of AmTA and washed just before virus inoculation, no inhibitory activity was seen; (c) a marked decrease of antiviral activity was observed when cultures were washed free of the compound two hours after virus inoculation: VR=0.7 versus 1.8 in unwashed cultures; (d) with both viruses, a significant inhibitory activity on CPE (VR=1.0) was still seen when AmTA was added to the cultures six hours after virus inoculation at a low multiplicity of infection (>0.01 TCID$_{50}$/cell), but the activity was marginal when the compound was added 24 hours after virus inoculation (VR=0.2). AmTA exerted no direct inactivating effect on the infectivity of Influenza A 2 virus when virus suspensions were incubated 1 hour at 37° C. with a 2.5 mg/ml solution in PBS of the compound.

Similar results were obtained with Encephalomyocarditis virus (EMC) strain V 77. LB 57 cells were grown in Eagle's minimum essential medium with 10% fetal cal serum. The timing of action of AmTA was studied using the plaque technique. The results of a typical experiment was 40 $\mu$g of AmTA/ml are summarized in Table 10. As with Herpes simplex, pretreatment and treatment during absorption were inactive. AmTA was active at a later stage of viral replication.

In vivo antiviral activity of AmTA was studied in several lethal infections of Charles River CD-1 adult mice. Table 11 summarized the results of a series of closely comparable experiments with murine encephalomyocarditis virus (EMC) strain ATCC VR 129: significant protection of the animals was seen when the compound was administered intraperitoneally (i.p.) or subcutaneously (s.c.) 1 hour before inoculation of 6–10 TCID$_{50}$/mouse, while oral treatments (p.o.) proved ineffective. The most effective dose was 50 mg/kg i.p., i.e. 15 times below the acute LD$_{50}$ of the compound for the mouse by this route and 7 times below its subacute LD$_{50}$ (5 consecutive daily treatments). The lowest dose causing weight loss is 5 times higher (250 mg/kg i.p.) but a slight and transient sedation is still seen at 60 mg/kg i.p. With a single treatment at 100 mg/kg i.p. (table 11) and, to a lesser degree at 50 mg/kg i.p., significant protection against EMC was still obtained when the mice received the compound 4 hours after virus inoculation, which is relatively late considering that, in this experimental system, untreated animals die within 4–5 days after virus inoculation. However, when mice were infected with EMC strain V77, protection with AmTA under similar experimental conditions was much less marked although still significant.

AmTA at the regimens found to be active on EMC virus infection, exerted no protective effect on the infection of mice with the following viruses: Herpes simplex (Virtue strain) inoculated i.p., i.v. or i.c.), Semliki Forest arbovirus (s.e.), West Nile arbovirus (i.p.), type C mouse-adapted foot-and-mouth disease virus (s.c. or i.p.), A 2/ANN Arbor/2/62 virus (aerosol). The compound was also inactive on Herpes simlex virus infection when administered at the same site as the virus (i.v. or i.c.) and on Influenza virus infection when given intranasally at 100 mg/kg repeatedly before and after virus inoculation.

In conclusion, AmTA has a broad spectrum of antiviral activity in cell cultures. Its mechanism of action is not known at the present time, but under our experimental conditions AmTA has no virucidal effect on these viruses and does not inhibit absorption and penetration of viruses.

In vivo, AmTA has been found repeatedly active only against murine leukemia viruses and EMC infections.

TABLE 9

| ANTIVIRAL ACTIVITY OF AmTA IN CELL CULTURE | | | |
|---|---|---|---|
| Virus+ | Cell substrate | Virus rating++ | ID$_{50}$+++ ($\mu$g/ml) |
| Adenovirus type 5 | KB | 1.7 | 11 |
| Coxsackie A-2 | WI-38 | 1.0 | 22 |
| Coronavirus (229E) | WI-38 | 0.4 | 125 |
| Equine rhinovirus | Monkey Kidney | 0.0 | — |
| Herpes simplex type I (HF) strain | Monkey Kidney | 1.2 | $\leqq$22 |
| Herpes simplex type I (HF) strain | WI-38 | 2.1 | $\leqq$11 |
| Influenza A2/HK/68++++ | Monkey Kidney | 1.5 | $\leqq$22 |
| Respiratory Syncytial virus (Long) | Monkey Kidney | 0.0 | — |
| Rhinovirus type 1A | WI-38 | 1.5 | $\leqq$22 |
| Rhinovirus type 1A | Monkey Kidney | 1.7 | $\leqq$11 |
| Rhinovirus type 1B | WI-38 | 2.3 | $\leqq$11 |

TABLE 9-continued

| ANTIVIRAL ACTIVITY OF AmTA IN CELL CULTURE | | | |
|---|---|---|---|
| Virus[+] | Cell substrate | Virus rating[++] | $ID_{50}$[+++] ($\mu g/ml$) |
| Vaccinia (WR) | Monkey Kidney | 0.6 | 125 |

[+] In each cell culture maintained in B—ME medium supplemented with 2% calf serum AmTA was added one hour before inoculation of 10 or 100 $TCID_{50}$ of the test virus at concentration of 125, 60, 30, 15, and 7$\mu g/ml$.
[++] VR is a measure of the inhibition of virus CPE by the compound at different concentrations, starting with the highest non-cytotoxic dose "Sidwell et al Science 1972, 177, 705". VR 1.0: marked antiviral activity; 0.9–0.5: moderate activity; 0.4–0.1: slight activity
[+++] Inhibiting dose 50%
[++++] Virus replication was followed by hemadsorption, not CPE in this case.

TABLE 10

EFFECT OF 21 TUNGSTO-9-ANTIMONIATE ON PLAQUE FORMATION BY EMC (STRAIN V77)

| Period of treatment | Number of plaques | Mean number of plaques | % inhibition | Statistical significance |
|---|---|---|---|---|
| No treatment | 41 - 28 - 31 - 29 | 32 | — | |
| 0–30 min | 39 - 20 - 35 - 34 - 31 | 32 | 0 | NS |
| 30 mn–24 hrs | 12 - 9 - 12 - 9 - 9 | 10 | 69 | P < 0.001 |
| 0–24 hrs. | 16 - 13 - 21 - 15 - 18 | 16 | 54 | P < 0.001 |

Time 0 is the time of virus inoculation; 40 $\mu g/ml$ of AmTA were added to the culture medium of treated groups.

TABLE 11

ON EMC ACUTE INFECTION OF MICE

| Untreated controls 4/120 (3.3%) | 100 mg/kg i.p. 1 treatment 54/85 (63.5%) (P 0.001) | 50 mg/kg i.p. 1 treatment 24/35 (68.5%) (P 0.001) | 50 mg/kg i.p. 3 treatments 31/45 (68%) (P 0.001) |
|---|---|---|---|
| 25 mg/kg i.p. 1 treatment 5/20 (25%) (P 0.001) | 100 mg/kg s.c. 3 treatments 13/30 (43.3%) (P 0.001) | 500 mg/kg p.o. 1 treatment 3/30 (10%) NS | 500 mg/kg i.p. 3 treatments 3/30 (10%) NS |

Statistical analysis was done using the chi square test.
1 treatment: 1
hr before virus s.c.
inoculation 3
treatments: 1
hr before 24
and 48 hrs
after virus
inoculation
Numbers refer to surviving mice over total infected mice.

TABLE 12

ACTIVITY OF AmTA on EMC VIRUS INFECTION OF MICE EFFECT OF A SINGLE TREATMENT AT VARIOUS INTERVALS

| Treatment performed | 100 mg/kg i.p. | 50 mg/kg i.p. | Untreated controls |
|---|---|---|---|
| 1 hr before virus inoculation | 21/30 (70%) P ≤ 0.001 | 9/15 (60%) P 0.001 | 4/30 (13.3%) |
| 4 hrs after virus inoculation | 18/30 (60%) P ≤ 0.001 | 4/15 (26%) NS | — |
| 24 hrs after virus inoculation NS | 3/30 (10%) NS | 0/15 (0%) | — |

Virus inoculated s.c.
Numbers refer to surviving mice over total infected mice.
Statistical analysis was done using the chi square test.

TABLE 13

PRELIMINARY RESULTS ON THE SENSIBILITY OF THE RABIES VIRUS WITH AMMONIUM 21-TUNGSTO-9-ANTIMONIATE SODATE IN VITRO AND IN VIVO

IN VITRO

1. Reduction of foci

The tungsto antimoniate inhibits the formation of foci on $BHK_{21}C_{13}S$ cells. The 50% inhibitory dose was found to be 4 $\mu g/ml$ when the ammoniate 21-tungsto-9-antimoniate sodate was added two hours after incubation of the virus. If it was added after 48 hours, it was not as efficient and at 72 hours, an increase of the number of plaques was noticed. A preincubation also inhibits the appearance of foci.

2. Cycle of replication (Table) (mechanism by which the genetic material is duplicated).

In a single cycle, with 20α of ammonium 21-tungsto-9-antimoniate sodate per ml, there was a reduction of about $10^1$ between 22 and 30 hours by counting plaques. With 50 α/ml, the difference from the control was about $10^2$.

IN VIVO

The toxic doses have been determined on mice by all the ways of inoculation. Protection is obtained by previous mixing of the inoculum with the ammonium 21-tungsto-9-antimoniate sodate. The 100% effective dose was of the order of 2.5 mg/mouse of 15 grams.

CONCLUSION

The sensibility of the rabies virus to the action of the ammonium 21-tungstate-9-antimoniate sodate is undeniable in vitro in the absence of any direct effect of the tungsto-antimoniate on the virus at efficient doses in vivo the results are encouraging.

TABLE 14

EFFECT OF HPA 23 ON INFECTION OF CD-1 ADULT MICE WITH VESICULAR STOMATITIS VIRUS (VSV) - INDIANA STRAIN -

Mice were inoculated intra-nasilly one half hour after a single intraperitoneal injection of HPA 23 at 50 or 100 mg/kg and the number of mice alive after 10 days was determined. The results are reported in the following Table.

| Product Administered | Dosage in mg/kg | Mean survival Time for dead mice | Mice alive 10 days after inoculation | Statistical significance |
|---|---|---|---|---|
| Controls | 0 | 5.9 ± 2.0 days | 1/25 | |
| HPA 23 | 100 | 8.2 ± 2.3 days | 12/25 | p < 0.001 |
| | 50 | 7.3 ± 2.4 days | 8/25 | p < 0.01 |

HPA 23 and murine interferon: synergism

Synergism occurs between HPA 23 and murine interferon to combat viral infections in mice. Mice received an intraperitoneal or intravenous injection of interferon and 5½ hours later received an intraperitoneal injection of 50 or 100 mg/kg of HPA 23. Thirty minutes later, the mice were innoculated with EMC virus, strain VR 125 and the results are reported in the following Table 15.

TABLE 15

| Treatment | Controls* No HPA 23 | HPA 23 50 mg/kg | HPA 23 100 mg/kg |
|---|---|---|---|
| Controls | 0/15* | 1/10 | 4/10 |

TABLE 15-continued

| Treatment | Controls*<br>No HPA 23 | HPA 23<br>50 mg/kg | HPA 23<br>100 mg/kg |
|---|---|---|---|
| no interferon | 3.1 ± 0.7 days** | 4.5 ± 1.9 days | 6.8 ± 2.6 days |
| Interferon undiluted 75.000 I.U./mouse i.p. | 5/10<br>7.1 ± 3.1 days | 9/10<br>9.4 ± 1.8 days | — |
| Interferon 1:3 25.000 I.U./mouse i.p. | 3/10<br>5.5 + 3.0 days | — | 7/10<br>8.2 ± 2.7 days |
| Interferon 1:9 8.000 I.U./mouse i.p. | 1/10<br>4.4 ± 2.1 days | — | — |
| Interferon undiluted 75.000 I.U./mouse i.v. | 6/10<br>7.7 ± 2.9 days | 10/10<br>≧10.0 days | — |

*Number of survival mice on inoculated mice
**range of death for dead mice

In a second test with an EMC virus, mice were given a murine interferon injection intraperitoneally or intravenously and were then infected with EMC virus six hours later. In some cases, the mice received HPA 23 thirty minutes before the infection and then the mice were observed for a period of time to determine the number of dead. The specific series of tests reported in the following Table 16 used following treatment of the animals. The tests E and L show a synergism between interferon and HPA 23 (results L).

TABLE 16

| | SURVIVAL MICE AFTER INFECTIONS EMC | | | | | | | | | |
|---|---|---|---|---|---|---|---|---|---|---|
| Days After Infection | A | B | C | D | E | F | G | H | K | L |
| 0 | 15 | 10 | 10 | 10 | 10 | 10 | 10 | 10 | 10 | 10 |
| 1 | 15 | 10 | 10 | 10 | 10 | 10 | 10 | 10 | 10 | 10 |
| 2 | 15 | 10 | 10 | 10 | 10 | 10 | 10 | 10 | 10 | 10 |
| 3 | 14 | 10 | 10 | 10 | 10 | 10 | 10 | 10 | 10 | 10 |
| 4 | 3 | 8 | 7 | 5 | 9 | 7 | 10 | 10 | 10 | 10 |
| 5 | 0 | 6 | 3 | 3 | 8 | 3 | 8 | 9 | 7 | 10 |
| 6 | | 6 | 3 | 2 | 6 | 1 | 4 | 9 | 7 | 10 |
| 7 | | 6 | 3 | 1 | 6 | 1 | 4 | 9 | 7 | 10 |
| 8 | | 5 | 3 | 1 | 6 | 1 | 4 | 9 | 7 | 10 |
| 9 | | 5 | 3 | 1 | 6 | 1 | 4 | 9 | 7 | 10 |
| 10 | | 5 | 3 | 1 | 6 | 1 | 4 | 9 | 7 | 10 |
| Definitively Survival | 0/15 | 5/10 | 3/10 | 1/10 | 6/10 | 1/10 | 4/10 | 9/10 | 7/10 | 10/10 |

TV = Controls virus
IF = Interferon
i.p. = by intra-peritoneal way
i.v. = by intra-venous way Various modifications of the products and processes of the invention may be made without departing from the spirit or scope thereof and it should be understood that the invention is to be limited only as defined in the appended claims.

We claim:

1. A pharmaceutical preparation for injection containing in sterile condition and in unit dosage form an antivirally effective amount of a non-toxic, pharmaceutically acceptable salt selected from the group consisting of alkali metal, alkaline earth metal and ammonium of 9-antimonio-III-21-tungsto VI sodate and a liquid pharmaceutical carrier.

2. A preparation as claimed in claim 1 and containing about 5 mg/ml of calcium phosphate.

3. A method of treating viral infections in mammals wherein the viruses are selected from the group consisting of leukemia viruses, sarcoma viruses, M-MSV virus, Friend's leukemia virus, plasma variant, sarcomatogenic viruses, encephalomyocardia virus, and rabies virus comprising administering to mammals by injection a sterile solution containing an antivirally effective amount of a non-toxic, pharmaceutically acceptable salt selected from the group consisting of alkali metal, alkaline earth metal and ammonium of 9-antimonio-III-21-tungsto VI sodate.

4. A method of treating viral infections in mammals wherein the viruses are selected from the group consisting of leukemia viruses, sarcoma viruses, M-MSV virus, Friend's leukemia virus, plasma variant, sarcomatogenic viruses, encephalomyocardia virus, and rabies virus comprising administering to mammals by injection an antivirally effective does of a non-toxic, pharmaceutically acceptable salt selected from the group consisting of alkali metal, alkaline earth metal and ammonium of 9-antimonio-III-21-tungsto-VI sodate.

5. A method for the prophylaxis or prevention of viral infections in mammals wherein the viruses are selected from the group consisting of leukemia viruses, sarcoma viruses, M-MSV virus, Friend's leukemia virus, plasma variant, sarcomatogenic viruses, encephalomyocardia virus, and rabies virus comprising administering by injection to a mammal subject to or shortly after exposure to virus infection an antivirally effective dose of a non-toxic, pharmaceutically acceptable salt selected from the group consisting of alkali metal, alkaline earth metal and ammonium of 9-antimonio-III-21-tungsto VI sodate.

* * * * *

UNITED STATES PATENT AND TRADEMARK OFFICE
CERTIFICATE OF CORRECTION

PATENT NO. : 4,547,369                                    Page 1 of 3

DATED     : Oct. 15, 1985

INVENTOR(S) : JEAN-CLAUDE CHERMANN, CLAUDE JASMIN, GEORGES MATHE, MARCEL RAYNAUD

It is certified that error appears in the above-identified patent and that said Letters Patent is hereby corrected as shown below:

| Col. | Line | | |
|---|---|---|---|
| [73] | | | |
| 1 | 59 | "r" should be --$\gamma$-- | |
| 1 | 60 | " " " " " " " " " " | |
| 2 | 1 | " " " " " " " " " " | |
| 12 | Table 9  34  Col. 4 | $<$ 22<br>$<$ 11<br>$<$ 22<br>$<$ 22<br>$<$ 11<br>$<$ 11 should be | $\leq$ 22<br>$\leq$ 11<br>$\leq$ 22<br>$\leq$ 22<br>$\leq$ 11<br>$\leq$ 11 |
| 12 | Under Col. 1 to 4  Left Out | --Herpes simples type I (virtue)    WI-38    1.2    22 | |
| 13 | Under Table 11 | Double Printing | |
| 13 | Table 12  2nd Col. | "P $\leq$ 0.001"  should be  --P $\leq$ 0.001--<br>"P $\leq$ 0.001"   " " " " " " " " " " | |
| 14 | Under Table 14  1st Col. | Double Printing | |
| 15 | Table 15  3rd Col. | " $\geq$ " | --$\geq$-- |

UNITED STATES PATENT AND TRADEMARK OFFICE
CERTIFICATE OF CORRECTION

PATENT NO. : 4,547,369                                Page 2 of 3
DATED : Oct. 15, 1985
INVENTOR(S) : JEAN-CLAUDE CHERMANN, CLAUDE JASMIN, GEORGES MATHE,
              MARCEL RAYNAUD It is certified that error appears in the above-identified patent and that said Letters Patent is hereby corrected as shown below:

Col.   Line   Page Line

Page 43   The Whole page missing

| Group | Treatment |
|---|---|
| A | Control-View only |
| B | Murine interferon 75.000 units/mouse<br>i.p. given 6 hours before the infection |
| C | Murine interferon 25.000 units/mouse<br>i.p. given 6 hourse before the infection |
| D | Murine interferon 8.000 units/mouse<br>i.p. given 6 hours before the infection |
| E | Murine interferon 75.000 units/mouse<br>i.p. given 6 hours before the infection |
| F | HPA-23 1 mg/mouse<br>i.p. given 30 minutes before the infection |
| G | HPA-23 2 mg/mouse<br>i.p. given 30 minutes before the infection |
| H | Murine interferon 75.000 units/mouse<br>i.p. given 6 hours before the infection +<br>HPA-23 1 mg/mouse, - 30 minutes |

UNITED STATES PATENT AND TRADEMARK OFFICE
CERTIFICATE OF CORRECTION

PATENT NO. : 4,547,369  Page 3 of 3

DATED : Oct. 15, 1985

INVENTOR(S) : JEAN-CLAUDE CHERMANN, CLAUDE JASMIN, GEORGES MATHE, MARCEL RAYNAUD

It is certified that error appears in the above-identified patent and that said Letters Patent is hereby corrected as shown below:

Col.   Line   Page   Line

Page 43 (Cont'd)

K             Murine interferon 25.000 units/mouse i.p. given 6 hours before the infection + HPA-23 2 mg/mouse, - 30 minutes L             Murine interferon 75.000 units/mouse i.v. given 6 hours before the infection + HPA-23 1 mg/mouse, - 30 minutes Signed and Sealed this First Day of July 1986

[SEAL]

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,547,369
DATED : Oct. 15, 1985
INVENTOR(S) : JEAN-CLAUDE CHERMANN, CLAUDE JASMIN, GEORGES MATHE, MARCEL RAYNAUD

It is certified that error appears in the above-identified patent and that said Letters Patent are hereby corrected as shown below:

On the title page assignee

[73]   "Cabinet Harle & Phelip" should be

--Agence Nationale De Valorisation De La Recherche (ANVAR) of Tour Aurore (92) Courbevoie, France--

Signed and Sealed this

Sixteenth Day of September 1986

[SEAL]

Attest:

DONALD J. QUIGG

Attesting Officer

Commissioner of Patents and Trademarks